(12) United States Patent
Cheng et al.

(10) Patent No.: US 7,569,590 B2
(45) Date of Patent: Aug. 4, 2009

(54) USE OF THIANECARBOXAMIDES AS DGAT INHIBITORS

(75) Inventors: Dong Cheng, Furlong, PA (US); Jeffrey T. Billheimer, West Chester, PA (US); James J. Devenny, Wayne, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/856,754

(22) Filed: Sep. 18, 2007

(65) Prior Publication Data

US 2008/0090876 A1    Apr. 17, 2008

Related U.S. Application Data

(60) Provisional application No. 60/845,651, filed on Sep. 19, 2006.

(51) Int. Cl.
  *A61K 31/44*  (2006.01)
  *A61K 31/496*  (2006.01)
(52) U.S. Cl. .................. 514/336; 514/255.05; 514/256; 514/909
(58) Field of Classification Search ................ 514/336, 514/255.05, 256, 909
  See application file for complete search history.

(56) References Cited

U.S. PATENT DOCUMENTS 5,491,152 A    2/1996    Wilde et al.

FOREIGN PATENT DOCUMENTS

WO    WO 2005044250 A1 *    5/2005

OTHER PUBLICATIONS

Chung et al., "Inhibition of Diacylglycerol Acyltransferase by Betulinic Acid from *Alnus hirsuta*", Planta Medica, vol. 72, No. 3, pp. 267-269 (Feb. 2006).*
Bell, R.M. et al., "Enzymes of Glycerolipid Synthesis in Eukaryotes", Ann. Rev. Biochem., vol. 49, pp. 459-487 (1980).
Cases, S. et al., "Cloning of DGAT2, a Second Mammalian Diacylglycerol Acyltransferase, and Related Family Members", The Journal of Biological Chemistry, vol. 276, No. 42, pp. 38870-38876 (2001).
Cases, S. et al., "Identification of a gene encoding an acyl CoA:diacylglycerol acyltransferase, a key enzyme in triacylglycerol synthesis", Proc. Natl. Acad. Sci. USA, vol. 95, pp. 13018-13023 (1998).
Chen, H.C. et al., "DGAT and Triglyceride Synthesis: A New Target for Obesity Treatment?", Trends Cardiovasc. Med., vol. 10, No. 5, pp. 188-192 (2000).
Chen, H.C. et al., "Increased insulin and leptin sensitivity in mice lacking acyl CoA:diacylglycerol acyltransferase 1", The Journal of Clinical Investigation, vol. 109, No. 8, pp. 1049-1055 (2002).
Lehner, R. et al., "Biosynthesis of Triacylglycerols", Prog. Lipid Res., vol. 35, No. 2, pp. 169-201 (1996).
Oelkers, P. et al., "Characterization of Two Human Genes Encoding Acyl Coenzyme A:Cholesterol Acyltransferase-related Enzymes", The Journal of Biological Chemistry, vol. 273, No. 41, pp. 26765-26771 (1998).
Orland, M.D. et al., "Acyl coenzyme A dependent retinol esterification by acyl coenzyme A:diacylglycerol acyltransferase 1", Biochimica et Biophysica Acta, vol. 1737, pp. 76-82 (2005).
Sliskovic, D.R. et al., Chapter 3: "ACAT Inhibitors: The Search for a Novel and Effective Treatment of Hypercholesterolemia and Atherosclerosis", Progress in Medicinal Chemistry, vol. 39, Elsevier Science B.V., publ., King, F.D. et al., eds., pp. 121-171 (2002).
Smith, S.J. et al., "Obesity resistance and multiple mechanisms of triglyceride synthesis in mice lacking Dgat", Nature Genetics, vol. 25, pp. 87-90 (2000).
Stone, S.J. et al., "Lipopenia and Skin Barrier Abnormalities in DGAT2-deficient Mice", The Journal of Biological Chemistry, vol. 279, No. 12, pp. 11767-11776 (2004).
Wilde, R.G. et al., "ACAT Inhibitors Derived from Hetero-Diels-Alder Cycloadducts of Thioaldehydes", Bioorganic & Medicinal Chemistry, vol. 4, No. 9, pp. 1493-1513 (1996).

* cited by examiner

*Primary Examiner*—Kevin E Weddington
(74) *Attorney, Agent, or Firm*—Terence J. Bogie

(57) ABSTRACT

The present application describes methods of treating obesity using DGAT-1 inhibitors according to Formula I:

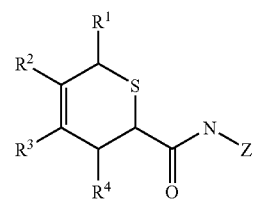

including all prodrugs, solvates, pharmaceutically acceptable salts and stereoisomers, wherein $R^1$, $R^2$, $R^3$, $R^4$ and Z are described herein.

2 Claims, No Drawings

USE OF THIANECARBOXAMIDES AS DGAT INHIBITORS

BACKGROUND

In mammals, there are two biochemical pathways for triacylglycerol synthesis: the monoacylglycerol pathway, which happens exclusively in the small intestine (R. Lehner and A. Kuksis, *Prog. Lipid Res.*, (1996) 35:169-201), and the glycerol-3-phosphate pathway, which takes place ubiquitously but most notably in the liver and in adipose tissue (R. M. Bell and R. A. Coleman, *Annu. Rev. Biochem.*, (1980) 49:459-487). The monoacylglycerol pathway initiates from acyl coenzyme A:monoacylglycerol acyltransferase (MGAT) (EC 2.3.1.22). Within minutes of its appearance from the digestion of dietary fat in the lumen of the small intestine, 2-monoacylglycerol is acylated by MGAT to form diacylglycerol. Diacylglycerol is further acylated by acyl coenzyme A:diacylglycerol acyltransferase (DOGAT) (EC 2.3.1.20) to re-synthesize triacylglycerol, which is packaged into chylomicron lipoprotein particles that eventually secreted into the lymph. In the glycerol-3-phosphate pathway, two fatty acyl coenzyme A molecules are added to glycerol-3-phosphate to form phosphatidate. These reactions are followed by the removal of the phosphate group by phosphatidate phosphohydrolase to generate diacylglycerol. Diacylglycerol is then further acylated by DGAT to form triacylglycerol. Collectively, DGAT lies at the final step of both triacylglycerol synthesis pathways.

Two DGAT enzymes have been identified, which are designated as DGAT1 and DGAT2 (S. Cases, S. J. Smith, Y. W. Zheng, H. M. Myers, S. R. Lear, E. Sande, S. Novak, C. Collins, C. B. Welch, A. J. Lusis, S. K. Erickson and R. V. Farese, Jr, *Proc. Natl. Acad. Sci. USA*, (1998) 95:13018-13023; P. Oelkers, A. Behari, D. Cromley, J. T. Billheimer and S. L. Sturley, *J. Biol. Chem.*, (1998) 273:26765-26771; S. Cases, S. J. Stone, P. Zhou, E. Yen, B. Tow, K. D. Lardizabal, T. Voelker and R. V. Farese, Jr., *J. Biol. Chem.*, (2001) 276: 38870-38876). Although they carry out identical enzymatic reactions, DGAT1 and 2 are encoded by two different genes that bear little sequence homology. Functionally, these two enzymes might have different physiological importance in vivo. DGAT1 knockout mice exhibit resistance towards the challenge of a high fat diet to become obese (S. J. Smith, S. Cases, D. R. Jensen, H. C. Chen, E. Sande, B. Tow, D. A. Sanan, J. Raber, R. H. Eckel and R. V. Farese, Jr., *Nat. Genet.*, (2000) 25:87-90). They are physically more active, possess a higher metabolic rate (H. C. Chen and R. V. Farese, Jr., *Trends Cardiovasc. Med.*, (2000) 10:188-192) and appear to have a greater insulin sensitive (H. C. Chen, S. J. Smith, Z. Ladha, D. R. Jensen, L. D. Ferreira, L. K. Pulawa, J. G. McGuire, R. E. Pitas, R. H. Eckel and R. V. Farese, Jr., *J. Clin. Invest.*, (2002) 109:1049-1055). In contrast, DGAT2 knockout mice exhibit phenotypes such as lipopenia and skin barrier abnormalities, resulting in death soon after birth (S. J. Stone, H. M. Myers, S. M. Watkins, B. E. Brown, K. R. Feingold, P. M. Elias and R. V. Farese, Jr., *J. Biol. Chem.*, (2004) 279:11767-11776).

DGAT1 belongs to the acyl coenzyme A:cholesterol acyltransferase (ACAT, EC 2.3.1.26) gene family. ACAT is the enzyme responsible for synthesis of cholesteryl ester using cholesterol and long-chain fatty acyl-coenzyme A as substrates. ACAT and DGAT have considerable biochemical similarities: both enzymes are proteins with multiple transmembrane domains and reside in the endoplasmic reticulum (ER). Both catalyze the reaction involving the transfer of an acyl-moiety of acyl coenzyme A to a hydrophobic substrate.

Both DGAT and ACAT have been considered as potential therapeutic targets. For DGAT, it has been proposed that inhibiting the synthesis of triacylglycerol would benefit in reducing weight, improve insulin sensitivity and reduce hepatic and circulating lipid content. For ACAT, it had been considered as a therapeutic target for cholesterol lowering and for anti-atherosclerosis.

During the past 20 years, numerous ACAT inhibitors have been developed (D. R. Sliskovic, J. A. Picard, B. R. Krause, "ACAT inhibitors: the search for a novel and effective treatment of hypercholesterolemia and atherosclerosis", *Prog. Med. Chem.*, (2002) 39:121-171). It is conceivable that due to the homology between ACAT and DGAT1, some ACAT inhibitors might possess DGAT inhibitory activities. Among them, thianecarboxamids are a series potent inhibitors that inhibits both hepatic and macrophage ACAT effectively (U.S. Pat. No. 5,491,152; R. G. Wilde, J. T. Billheimer, S. J. Germain, E. A. Hausner, P. C. Meunier, D. A. Munzer, J. K. Stoltenborg, P. J. Gillies, D. L. Burcham, S. M. Huang, J. D. Klaczkiewicz, S. S. Ko, R. R. Wexler, "ACAT inhibitors derived from hetero-Diels-Alder cycloadducts of thioaldehydes", *Bioorg. Med. Chem.*, (1996) 4:1493-1513). In the current invention, we provide evidence that this chemical series indeed possess potent inhibitory activities against DGAT.

DETAILED DESCRIPTION

The present application provides methods for using the compounds according to Formula I either alone or in combination with another therapeutic agent to treat a patient in need, specifically a patient suffering from obesity.

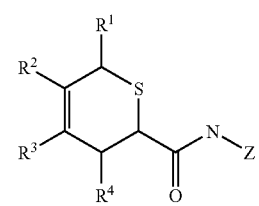

I wherein

Z is selected from the group consisting of aryl and heteroaryl, wherein each aryl and heteroaryl may be optionally substituted with 1 to 3 $R^5$;

$R^1$, $R^2$, $R^3$ and $R^4$ are independently selected from the group consisting of alkyl and alkoxy, wherein $R^3$ and $R^4$ may be taken together to form an aryl ring that is optionally substituted with 1 to 3 $R^6$;

$R^5$ is selected from the group consisting of alkyl, thioalkyl and halo; and $R^6$ is selected from the group consisting of alkyl and alkoxy.

DEFINITIONS

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, mercapto or thio, cyano, alkylthio, cycloalkyl, heterocyclyl, aryl, heteroaryl, carboxyl, carbalkoyl, carboxamido, carbonyl, alkenyl, alkynyl, nitro, amino, alkoxy, aryloxy, arylalkyloxy, heteroaryloxy, amido, —OPO$_3$H, —OSO$_3$H, and the like to form alkyl groups such as trifluoromethyl, 3-hydroxyhexyl, 2-carboxypropyl, 2-fluoroethyl, carboxymethyl, cyanobutyl and the like.

The term "alkoxy" as employed herein alone or as part of another group includes an alkyl or group as defined above linked through an oxygen atom.

The term "halogen" or "halo" as used herein alone or as part of another group refers to chlorine, bromine, fluorine and iodine, with bromine, chlorine or fluorine being preferred.

The term "thio" as used herein as part of another group refers to a sulfur atom serving as a linker between two groups such as, for example, thioalkyl.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, for example

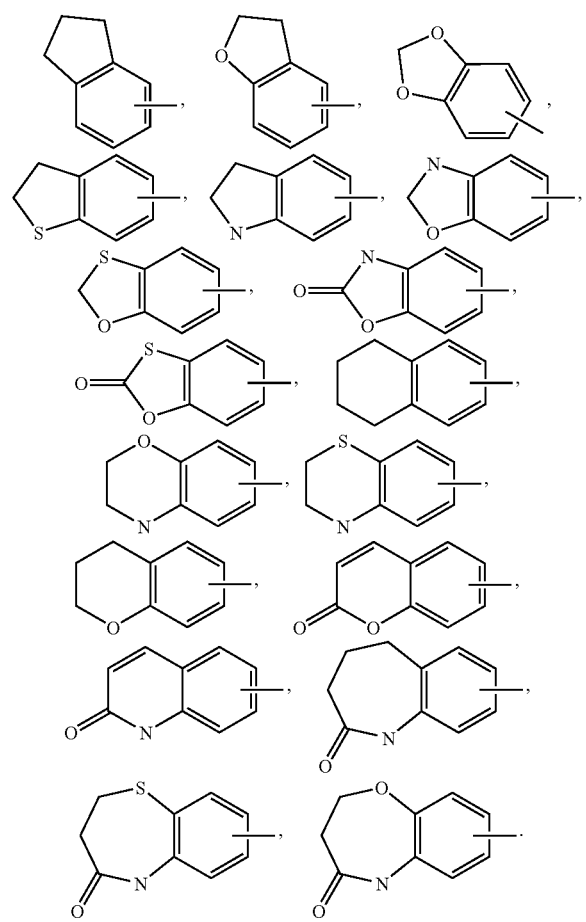

Further, "aryl", as defined herein, may optionally be substituted with one or more functional groups, such as halo, alkyl, haloalkyl, alkoxy, haloalkoxy, alkenyl, alkynyl, cycloalkyl, cycloalkylalkyl, heterocyclyl, heterocycloalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxyl, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in A. R. Katritzky and C. W. Rees, eds. *Comprehensive Heterocyclic Chemistry: The Structure, Reactions, Synthesis and Uses of Heterocyclic Compounds*(1984) Pergamon Press, New York, N.Y.; and A. R. Katritzky, C. W. Rees, E. F. Scriven, eds. *Comprehensive Heterocyclic Chemistry II: A Review of the Literature 1982-1995* (1996) Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

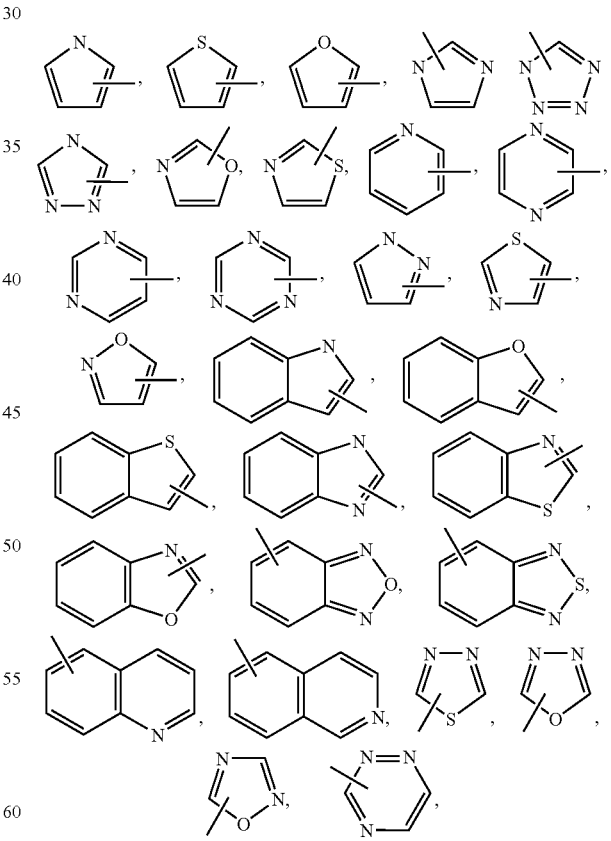

and the like.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "bioactive metabolite" as employed herein refers to any functional group contained in a compound of formula I with an open valence for further substitution wherein such substitution can, upon biotransformation, generate a compound of formula I. Examples of such functional groups of bioactive metabolites include, but are not limited to, —OH, —NH or functional groups wherein the hydrogen can be replaced with a functional group such as —$PO_3H_2$ for example, which, upon biotransformation generates an —OH or —NH functional group of a compound of formula I.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. Prodrug esters may also include—but are not limited to groups such as phosphate esters, phosphonate esters, phosphonamidate esters, sulfate esters, sulfonate esters, and sulfonamidate esters wherein the ester may be further substituted with groups that confer a pharmaceutical advantage such as—but not limited to—favorable aqueous solubility or in vivo exposure to the bioactive component formula I.

The term "prodrug" as employed herein includes functionalization of bioactive amine- or hydroxyl-containing compounds of formula I to form alkyl-, acyl-, sulfonyl-, phosphoryl-, or carbohydrate-substituted derivatives. Such derivatives are formed by reacting compounds of formula I with alkylating-, acylating-, sulfonylating-, or phosphorylating reagents employing procedures known to those skilled in the art. Alkylation of amines of formula I may result in—but are not limited to—derivatives that include spacer units to other prodrug moieties such as substituted alkyoxymethyl-, acyloxymethyl-, phosphoryloxymethyl-, or sulfonyloxymethyl-groups. Alkylation of amines of formula I may result in the generation of quarternary amine salts that act in vivo to provide the bioactive agent (i.e., the compound of formula I).

Preferred prodrugs consist of a compound of formula I where a pendant hydroxyl is phosphorylated to generate a phosphate derivative. Such a prodrug may also include a spacer group between the compound of formula I and the phosphate group, such as a methyleneoxy-group. Methods to generate such a prodrug from a compound of formula I are known to those skilled in the art, and are listed in the references below.

Preferred prodrugs also consist of a compound of formula I where a pendant amine, such as a pyridine group, is alkylated with a group, such as methyl, to form a quarternary ammonium ion salt. Methods to generate such a prodrug from a compound of formula I are known to those skilled in the art, and are listed in the references below.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

(a) *The Practice of Medicinal Chemistry*, Camille G. Wermuth et al., Ch. 31 (Academic Press, 1996);

(b) *Design of Prodrugs*, edited by H. Bundgaard (Elsevier, 1985);

(c) *A Textbook of Drug Design and Development*, P. Krogsgaard-Larson and H. Bundgaard, eds. Ch. 5, pp. 113-191 (Harwood Academic Publishers, 1991);

(d) *Hydrolysis in Drug and Prodrug Metabolism*, B, Testa and J. M. Mayer, (Verlag Helvetica Chimica Acta AG, Zurich, Switzerland; Wiley-VCH, Weinheim, Federal Republic of Germany, 2003);

(e) P. Ettmayer, G. L. Amidon, B. Clement, B. Testa, "Lessons Learned from Marketed and Investigational Prodrugs", *J. Med. Chem.*, (2004) 47(10):2393-2404; and (f) S. K. Davidsen et al. "N-(Acyloxyalkyl)pyridinium Salts as Soluble Prodrugs of a Potent Platelet Activating Factor Antagonist", *J. Med. Chem.*, (1994) 37(26):4423-4429.

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques, chiral HPLC or fractional crystallization.

EXAMPLES

The syntheses of the following examples are described in U.S. Pat. No. 5,491,152 (hereinafter "the '152 patent"), which is incorporated herein by reference.

Example 1

Table 1, Column 83, Example 31, the '152 Patent

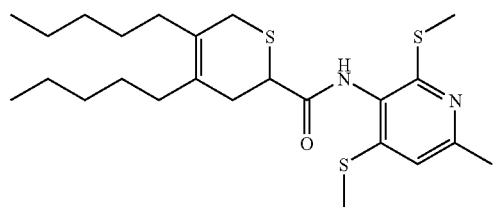

Example 2

Table 1, Column 83, Example 66, the '152 Patent

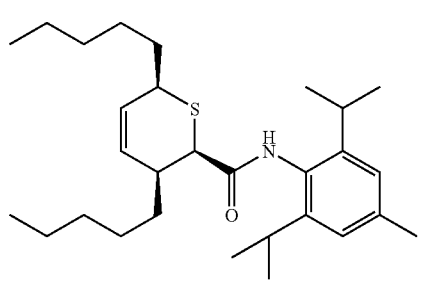

Example 3

Table 1, Column 83, Example 67, the '152 Patent

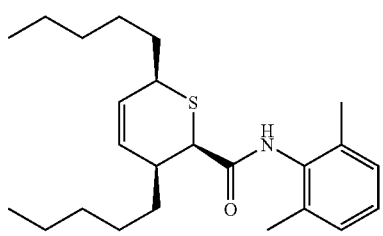

Example 4

Column 52, Line 19 to Column 56, Line 22, the '152 Patent

Table 1, Column 85, Example 70, the '152 patent

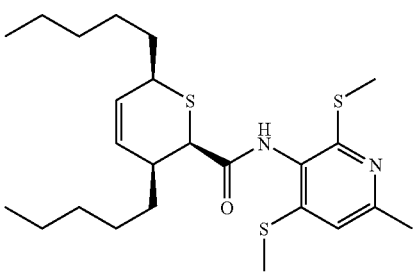

Example 5

Table 1, Column 83, Example 36, the '152 Patent

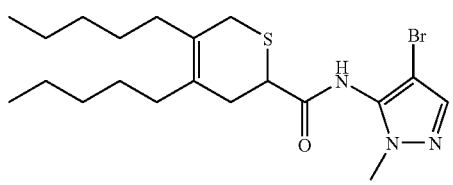

Example 6
Table 6, Column 117, Example 610, the '152 Patent
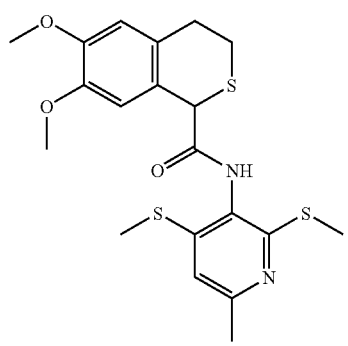
Example 7
Table 6, Column 117, Example 606, the '152 Patent
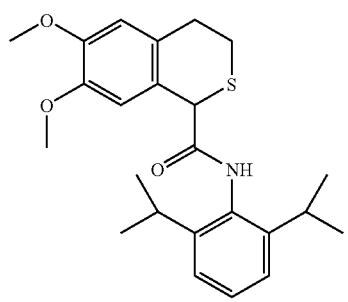
Example 8
Table 6, Column 119, Example 666, the '152 Patent
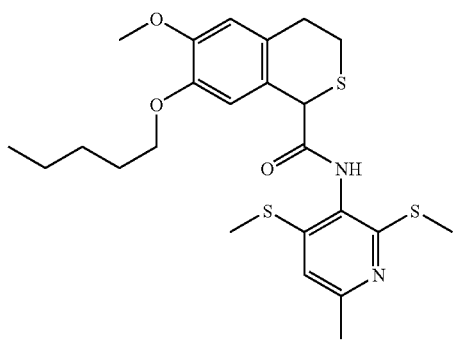
Example 9
Table 6, Column 119, Example 662, the '152 Patent
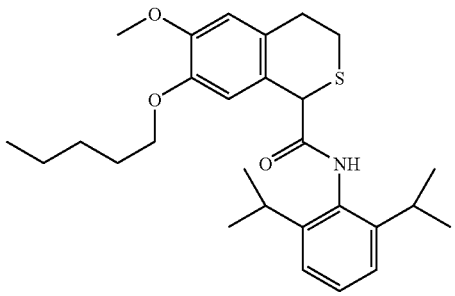
Example 10
Column 52, Line 19 to Column 56, Line 22, the '152 Patent
Table 1, Column 85, Example 70, the '152 Patent
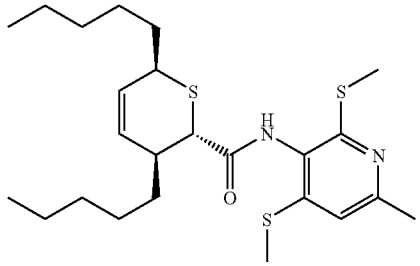
Example 11
Table 1, Column 87, Example 140, the '152 Patent
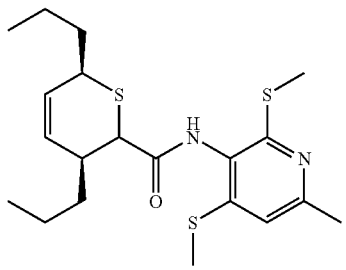

Example 12

Table 1, Column 87, Example 144, the '152 Patent

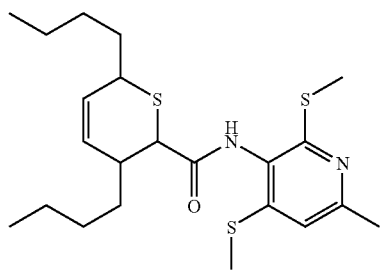

Example 13

Table 1, Column 87, Example 148, the '152 Patent

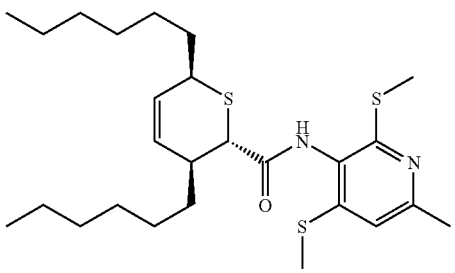

Biological Evaluation

To perform DGAT assays, aliquots of 10 μg microsome derived from rat adipose tissues were preincubated with either DMSO or various test compounds (final vehicle DMSO concentration at 2.5%) in 190 μl of Assay Buffer (175 mM, pH7.8, 1 mg/ml BSA, 8 mM $MgCl_2$, 160 μM, 1,2-dioleoylglycerol (delivered by acetone, final vehicle concentration 5%, v/v) for 10 min in a water bath at 23° C. The DGAT reaction was initiated by adding 10 μl of 10 nmol [$^{14}$C]oleoyl-CoA (specific activity 10,000 dpm/nmol). After incubating for 10 min at 23° C., the reaction was terminated by addition of 6 ml of chloroform/methanol (2:1, v/v). An internal standard with carrier ([$^3$H]triolein, 200 dpm/μl, 1 μg/μl in toluene) was added to determine the recovery of triglyceride in the subsequent steps. To facilitate phase separation, 1.2 ml of water was added, mixed and allowed to sit at room temperature for more than 2 hrs. The aqueous phase was discarded and the organic phase containing the lipids was dried under $N_2$, resuspended in 100 μl chloroform and spotted on ITLC-SA thin layer plates (Gelman Sciences). Lipids were separated by thin layer chromatography using solvent system of hexane:diethyl ether:acetic acid (85:15:0.5) for 20 min. The lipids were visualized by iodine staining and the triglyceride band was cut from the plate and subjected to scintillation counting. Specific DGAT activity was calculated as nmol/min/mg protein. The percent of inhibition by test compound is calculated by equation (1):

Percent inhibition=(DGAT activity with DMSO−DGAT activity with test compound)/(DGAT activity with DMSO)×100

TABLE I

Inhibition of DGAT activity

| Example | % control |
|---|---|
| 1 | 17 |
| 2 | 4 |
| 3 | 46 |
| 4 | 4 |
| 5 | 45 |
| 6 | 4 |
| 7 | 5 |
| 8 | 3 |
| 9 | 21 |
| 10 | 11 |
| 11 | 10 |
| 12 | 6 |
| 13 | 9 |

Utilities Combinations

A. Utilities

The compounds of the present invention are DGAT modulators, and include compounds which are, for example, activators or inhibitors of DGAT enzyme. Accordingly, the compounds of the present invention may be useful for the treatment or prevention of diseases and disorders associated with DGAT enzyme activities. Preferably, compounds of the present invention possess activity as inhibitors of DGAT enzyme activities, and may be used in the treatment of diseases or disorders associated with the activity of the DGAT enzyme.

Accordingly, the compounds of the present invention can be administered to mammals, preferably humans, for the treatment of a variety of conditions and disorders, including, but not limited to metabolic as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashinoto's thyroiditis; Guillain-Barre syndrome; cancer; contact dermatitis; allergic rhinitis; and ischemic or reperfusion injury.

The present invention contains compounds that possess both DGAT and ACAT inhibitory activities. ACAT inhibition is a known mechanism to provide hypolipidemic effects (which also has anti-atherosclerosis activity) such as disclosed in, *Drugs of the Future*, 24:9-15 (1999) (Avasimibe); "The ACAT inhibitor, Cl-1011 is effective in the prevention and regression of aortic fatty streak area in hamsters", Nicolosi et al., *Atherosclerosis* (Shannon, Irel), 137(1):77-85 (1998); "The pharmacological profile of FCE 27677: a novel ACAT inhibitor with potent hypolipidemic activity mediated by selective suppression of the hepatic secretion of ApoB1100-containing lipoprotein", G. Ghiselli, *Cardiovasc. Drug Rev.*, 16(1): 16-30 (1998); "RP 73163: a bioavailable alkylsulfinyl-diphenylimidazole ACAT inhibitor", C. Smith et al., *Bioorg. Med. Chem. Lett.*, 6(1):47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred, A., *Inflammation: Mediators Pathways*, 173-198 (1995), Publisher: CRC, Boca Raton, Fla.; "ACAT inhibitors: potential anti-atherosclerotic agents", Sliskovic et al., *Curr. Med. Chem.*, 1(3):204-125 (1994); "Inhibitors of acyl-CoA: cholesterol O-acyl transferase (ACAT) as hypocholester-olemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.*, 8(6):359-362 (1995), or TS-962 (Taisho Pharmaceutical Co. Ltd), as well as F-1394, CS-505, F-12511, HL-004, K-10085 and YIC-C8-434. Compounds of the current invention therefore is particularly useful in treating obesity and hyperlipidemia and atherosclerosis.

The present invention further relates to the use of a DGAT inhibitor for the treatment of bulimia and obesity, including obesity associated with type II diabetes (non-insulin-dependent diabetes), or more generally any disease resulting in the patient becoming overweight. Obesity, as described herein, is defined by a body mass index (kg/m$^2$) of at least 26. It may be due to any cause, whether genetic or environmental, including overeating and bulimia, polycystic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

As modulators of the DGAT enzyme, the compounds of the present invention are further useful for the treatment and prevention of respiratory diseases and disorders. Respiratory diseases for which DGAT modulators are useful include, but are not limited to, chronic pulmonary obstructive disorder, emphysema, asthma, and bronchitis. In addition, DGAT modulators block the activation of lung epithelial cells by moieties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ischemia/reperfusion injury); dermatomyositis; alopecia greata; chronic actinic dermatitis; eczema; Behoet's disease; Pustulosis palmoplanteris; Pyoderma gangrenum; Sezary's syndrome; atopic dermatitis; systemic sclerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

DGAT is important in the regulation of TNF alpha of adipocytes. Compounds of the present invention is especially of value, for example, in treating obesity associated inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the DGAT inhibitors in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR δ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-IB inhibitor).

The antidiabetic agent may be an oral antihyperglycemic agent preferably a biguanide such as metformin or phenformin or salts thereof preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594, 016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in K. Yajima et al., *Am. J. Physiol. Endocrinol. Metab.,* 284:E966-E971 (2003)), AZ-242 (tesaglitazar; Astra-Zeneca; as described in B. Ljung et al., *J. Lipid Res.,* 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an FMGO CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.,* 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in S. A. Biller, K. Neuenschwander, M. M. Ponpipom and C. D. Poulter, *Current Pharmaceutical Design,* 2:1-4.0 (1996).

In addition, other squalene synthetase inhibitors suitable for use herein include the terpenoid pyrophosphates disclosed by P. Ortiz de Montellano et al., *J. Med. Chem.,* 20:243-249 (1977), the farnesyl diphosphate analog A and presqualene pyrophosphate (PSQ-PP) analogs as disclosed by Corey and Volante, *J. Am. Chem. Soc.*, 98:1291-1293 (1976), phosphinylphosphonates reported by R. W. McClard et al., *J. Am. Chem. Soc.*, 109:5544 (1987) and cyclopropanes reported by T. L. Capson, Ph.D., dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH148461 (ezetimibe) as well as those disclosed in *Atherosclerosis* 115:45-63 (1995) and *J. Med. Chem.* 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na$^+$/bile acid cotransporter inhibitor such as disclosed in Drugs of the Future, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

DGAT inhibitors could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, 1MPDH inhibitors, such as mycophenolate (CellCept®), integrin antagonists, alpha-4 beta-7 integrin antagonists, cell adhesion inhibitors, interferon gamma antagonists, CAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogenactivated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with DGAT inhibitors include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or TL-4 receptor fusion proteins and PDE 4 inhibitors such as Ariflo, and the PTK inhibitors disclosed in the following U.S. patent applications, incorporated herein by reference in their entirety. Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: D. Hollenbaugh et al., "Cleavable CD40Ig Fusion Proteins and the Binding to Sgp39", *J. Immunol. Methods* (Netherlands), 188(1):1-7 (Dec. 15, 1995); D. Hollenbaugh et al., "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J* (England), 11(12):4313-4321 (December 1992); and L. W. Moreland et al., "Treatment of Rheumatoid Arthritis with a Recombinant Human Tumor Necrosis Factor Receptor (P75)-Fc Fusion Protein", *New England J. of Medicine,* 337 (3):141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula (I) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably up to 100 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A method for treating obesity, comprising: administering a therapeutically effective amount of at least one DGAT-1 inhibitor compound, or a pharmaceutically acceptable salt or a stereoisomer thereof, to a patient in need of a treatment for obesity, wherein the at least one DGAT-1 inhibitor compound is a compound of Formula I;

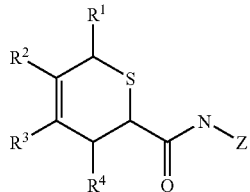

wherein

Z is selected from the group consisting of aryl and heteroaryl, wherein each aryl and heteroaryl may be optionally substituted with 1 to 3 $R^5$;

$R^1$, $R^2$, $R^3$ and $R^4$ are independently selected from the group consisting of alkyl and alkoxy, wherein $R^3$ and $R^4$ may be taken together to form an aryl ring that is optionally substituted with 1 to 3 $R^6$;

$R^5$ is selected from the group consisting of alkyl, thioalkyl and halo; and $R^6$ is selected from the group consisting of alkyl and alkoxy.

2. A method for treating obesity, comprising: administering a therapeutically effective amount of at least one DGAT-1 inhibitor compound, or a pharmaceutically acceptable salt or a stereoisomer thereof, to a patient in need of a treatment for obesity, wherein the at least one DGAT-1 inhibitor compound is a compound selected from the group consisting of:

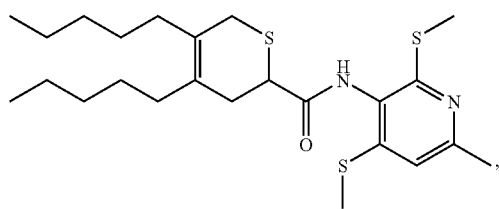

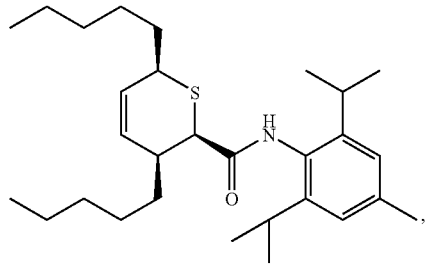

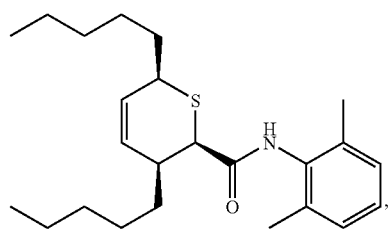

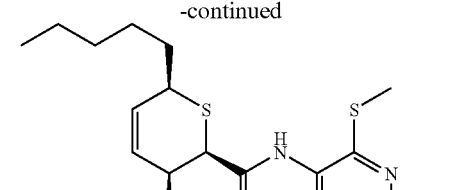

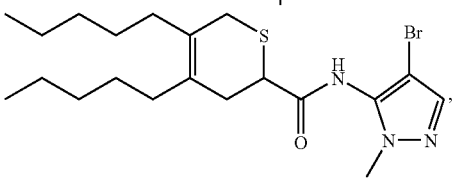

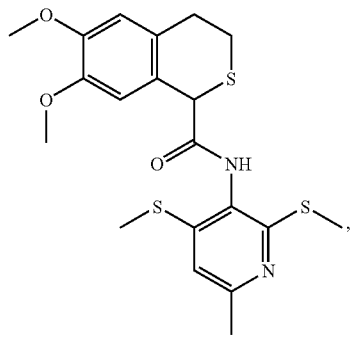

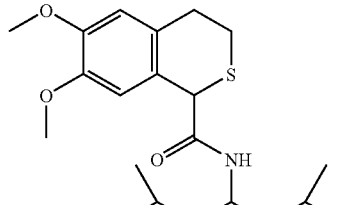

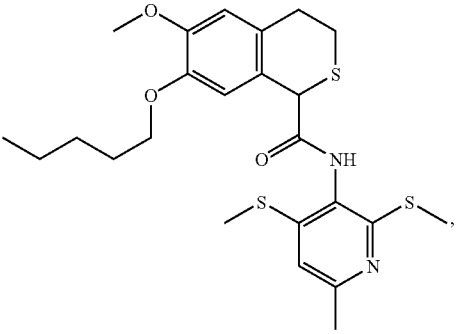

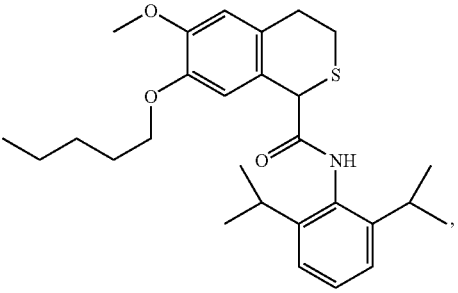

-continued
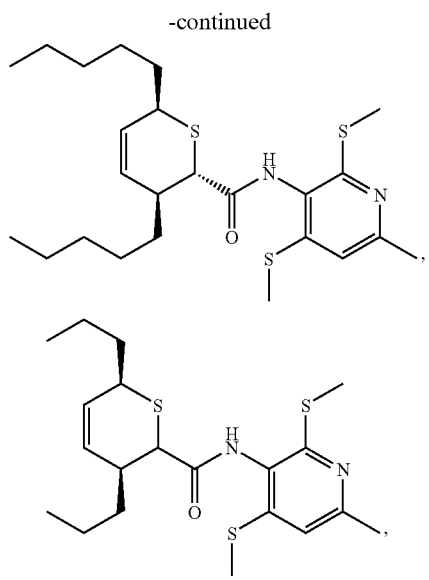
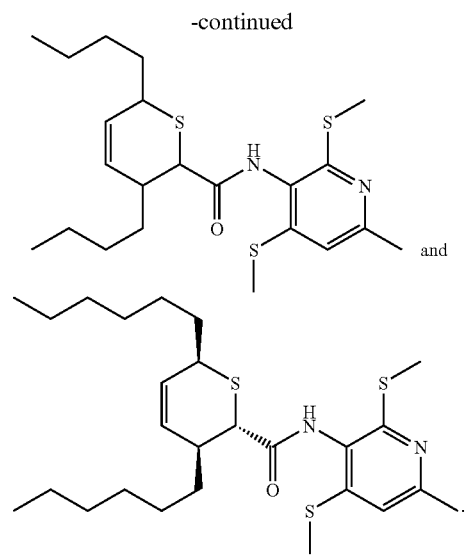
* * * * *